(12) United States Patent
Mendoza

(10) Patent No.: US 11,488,692 B2
(45) Date of Patent: *Nov. 1, 2022

(54) EMERGENCY DEPARTMENT COMMUNICATION SYSTEM

(71) Applicant: Central Line Health, LLC, Chicago, IL (US)

(72) Inventor: Carrie D. Mendoza, Glencoe, IL (US)

(73) Assignee: CurieHealth, Inc., Chicago, IL (US)

(*) Notice: Subject to any disclaimer, the term of this patent is extended or adjusted under 35 U.S.C. 154(b) by 770 days.

This patent is subject to a terminal disclaimer.

(21) Appl. No.: 15/941,884

(22) Filed: Mar. 30, 2018

(65) Prior Publication Data

US 2019/0304576 A1 Oct. 3, 2019

(51) Int. Cl.
*G16H 10/60* (2018.01)
(52) U.S. Cl.
CPC .................... *G16H 10/60* (2018.01)
(58) Field of Classification Search
CPC ........ G16H 10/60; G16H 20/17; G16H 40/20; G16H 40/67
See application file for complete search history.

(56) References Cited

U.S. PATENT DOCUMENTS

| | | | | |
|---|---|---|---|---|
| 10,493,014 | B2* | 12/2019 | Murphy | A61L 27/52 |
| 2005/0108057 | A1* | 5/2005 | Cohen | G16H 40/20 |
| | | | | 705/3 |
| 2012/0088222 | A1* | 4/2012 | Considine | G09B 5/00 |
| | | | | 434/362 |
| 2018/0366021 | A1* | 12/2018 | Zertuche | G09B 7/00 |

* cited by examiner

*Primary Examiner* — Reginald R Reyes

(57) ABSTRACT

The disclosed technology addresses the need in the art for an enhanced communication system for emergency departments. A system is configured to receive, from an emergency department device, registration information for a patient device, generate a unique identifier associated with the registration information, and provide the unique identifier to the emergency department device. The system is further configured to receive, from the patient device, a communication including the unique identifier and contact information and store, based on the communication, an entry for the patient device in a device database, wherein the entry for the patient device comprises the registration information and the contact information.

20 Claims, 13 Drawing Sheets

100

EMERGENCY DEPARTMENT COMMUNICATION SYSTEM

TECHNICAL FIELD

The present disclosure pertains to electronic communication technologies, and more specifically to a communication system for use in an emergency department or hospital setting.

BACKGROUND

Various electronic communication technologies such as short message service (SMS) text messaging, email, or messaging applications provide various means for users to communicate with one another generally. Furthermore, many of these technologies are conveniently available on mobile devices such as smart phones or tablets. However, existing technologies are not appropriate for all settings. For example, in the medical setting, and in particular in the context of emergency department or emergency room waiting areas, there exist a number of technological obstacles that prevent the adoption of available communication solutions.

BRIEF DESCRIPTION OF THE DRAWINGS

The above-recited and other advantages and features of the disclosure will become apparent by reference to specific embodiments thereof which are illustrated in the appended drawings. Understanding that these drawings depict only example embodiments of the disclosure and are not therefore to be considered to be limiting of its scope, the principles herein are described and explained with additional specificity and detail through the use of the accompanying drawings in which.

DESCRIPTION OF EXAMPLE EMBODIMENTS

Figure 1:
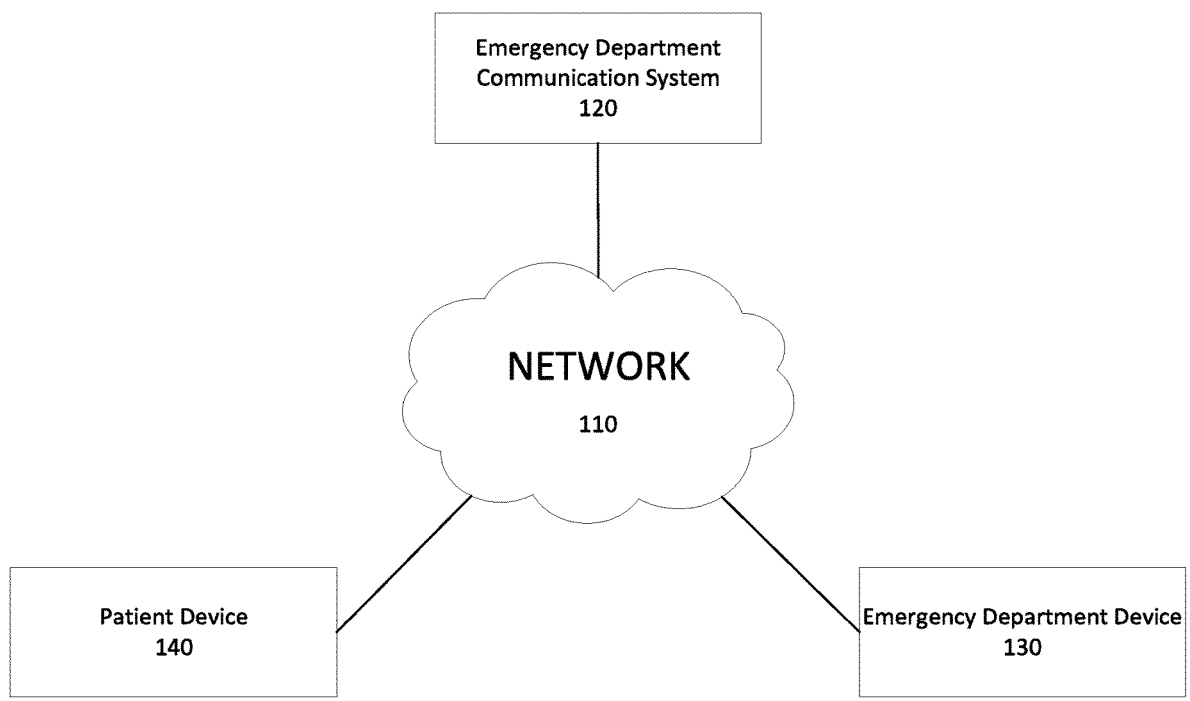
FIG. 1 is a conceptual block diagram illustrating an example network environment, in accordance with various embodiments of the subject technology.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure.

Emergency departments in medical facilities, such as hospitals, present a different set of circumstances in which existing communication technologies are not well suited for. Accordingly, many emergency departments do not communicate with patients and their surrogates using electronic means. For example, the Health Insurance Portability and Accountability Act of 1996 (HIPAA) establishes policies and standards for maintaining the privacy and the security of individually identifiable health information and establishes severe civil and criminal penalties for violations. Existing communication solutions have technical shortcomings in their technologies that do not adequately meet the policies and standards established by HIPAA or are unable to meet the policies and standards with sufficient certainty to be adopted.

Regardless of the legal requirements for privacy and security in a communications system, existing communication solutions lack a secure means for registration and communication with patients. Furthermore, patients often are accompanied by companions (e.g., surrogates, family members, assistants, caregivers, etc.). Existing communication solutions do not adequately maintain the privacy and security of private information or adequately manage a patient's consent for companions to receive communications regarding the patient.

Lack of an effective communication system in emergency department settings results in patients leaving without being seen because of poor wait time management, inefficiencies in work flow causing fewer patients to be seen, or losses from lawsuits stemming from poor communications in the emergency department. Additionally, there may be penalties from value based purchasing (VBP) schemes where fees recouped by emergency department depend on patient satisfaction scores and other measures of service and effectiveness. These factors may result in a significant loss of income for an emergency department.

The disclosed technology address the need in the art for a more effective and appropriate means of electronic communications between members of the emergency department team and patient teams (e.g., family members or other companions, caregivers, assistants, surrogates, or any other patient authorized entity).

The emergency department communication system disclosed may provide for more convenient and efficient means for emergency department team members to communicate with patient teams while also providing improved patient satisfaction. In fact, a recent survey has shown that 81% of patients felt that the emergency department communication system improved their emergency department experience while an additional 10.1% of patients felt that the emergency department communication system somewhat improved their emergency department experience. Additionally, 84.8% of the patients felt that they were better informed because of the communications received from the emergency department communication system while an additional 5.1% felt somewhat better informed. Patient satisfaction scores, such as these, may have a direct impact on hospital revenue, compliance, and compensation for doctors or other emergency department team members.

FIG. 1 is a conceptual block diagram illustrating an example network environment 100, in accordance with various embodiments of the subject technology. The network environment 100 includes an emergency department communication system 120, one or more emergency department device 130, and one or more patient devices. Although various embodiments disclosed herein relate to the emergency department setting, other embodiments may relate to other in-hospital settings.

Although FIG. 1 illustrates a client-server network environment 100, other embodiments of the subject technology may include other configurations including, for example, peer-to-peer environments or single-system environments. For example, although FIG. 1 shows emergency department communication system 120 as a single entity, in some embodiments, emergency department communication system 120 may be implemented as a number of distinct entities. Furthermore, in some embodiments, emergency department communication system 120 may provide a cloud service for emergency department devices 130 and/or the patient devices 140 and be implemented in a separate computing unit from emergency department devices 130. However, in other embodiments, emergency department communication system 120 may be implemented wholly or partially on one or more emergency department devices 130.

The emergency department communication system 120, the emergency department devices 130, and the patient devices 140 may communicate via a network 110. The network 110 can be any type of communication network and may include, for example, any one or more of a cellular network, a satellite network, a personal area network (PAN), a local area network (LAN), a wide area network (WAN), an enterprise network, the Internet, and the like. Network can be a public network, a private network, or a combination thereof. Communication network may be implemented using any number of communications links associated with one or more service providers, including one or more wired communication links, one or more wireless communication links, or any combination thereof. Additionally, network can be configured to support the transmission of data formatted using any number of protocols.

The one or more emergency department devices 130 may be configured to allow emergency department team members (e.g., doctors, nurses, technicians, clinicians, assistants, or other emergency department personnel) to access and update patient information, select patients to interact with, and transmit messages to patient devices. These actions may be performed via a communication system dashboard provided by the emergency department communication system 120. The emergency department devices 130 may be, for example, a computer, a smartphone, a tablet, a wearable device, or other computing device configured to provide an interface between the emergency department communication system 120 and an emergency department team member. Although various aspects of the subject technology relate to a visual communication system dashboard displayed on an emergency department device 130, other types of interfaces (e.g., an audio interface provided by a digital voice assistant) may also be additionally or alternatively used.

The one or more patient devices 140 may be configured to allow patients or patient authorized individuals (e.g., family members or other companions, caregivers, assistants, or surrogates) to receive and view messages transmitted by emergency department team members. The patient devices 140 may be, for example, smart phones, laptops or other computing devices, wearable devices, or other communication devices.

The emergency department communication system 120 is configured to manage communications between the emergency department devices 130 and the patient devices 140. As is described in further detail throughout, the emergency department communication system 120 is configured to interact with the emergency department devices 130, the patient devices 140, and potentially other entities in order to securely register patient devices 140 to receive communications from at least one emergency department device 130 in a manner that maintains the privacy of patient data and is compliant with HIPAA and/or other standards.

Once a patient device 140 is registered, the emergency department communication system 120 provides an interface (e.g., a dashboard) for one or more emergency department devices 130 to communicate with the registered patient device 140. Communications sent via the emergency department communication system 120 may include, for example, messages from emergency department team members greeting patients, introducing one or more members of the emergency department team, or providing an overview of processes (e.g., for intake, treatment, etc.). Messages may further provide an estimate of remaining waiting time, a notification of certain events, progress, or unexpected delays, or any other information which emergency department team members might wish to communicate with patients or patient authorized individuals. The communications may include text, images, videos, audio, links to websites or other universal resource locators (URLs), files, or other types of content.

Some embodiments allow for only one-way communications from emergency department devices 130 to patient devices 140 and the patient devices 140 are unable to transmit messages to an emergency department device 130. These embodiments reduce the legal liability associated with receiving certain patient related messages and/or responding to patient related messages. For example, any delay in responding to some patient messages may open up emergency departments to liability should unfortunate results occur even if the delay can be considered by some to be reasonable or within normal operating limitations.

Accordingly, these embodiments restrict patient devices 140 from communicating with emergency department devices via the emergency department communication system 120. Instead, patients or members of a patient team can communicate with emergency department personnel in person or through other means. Other embodiments, however, do allow for two-way communications between the emergency department devices 130 and the patient devices 140. For example, the emergency department communication system 120 may provide an interface for a registered patient device 140 to transmit messages or other content to one or more emergency department devices 130.

Figure 2:
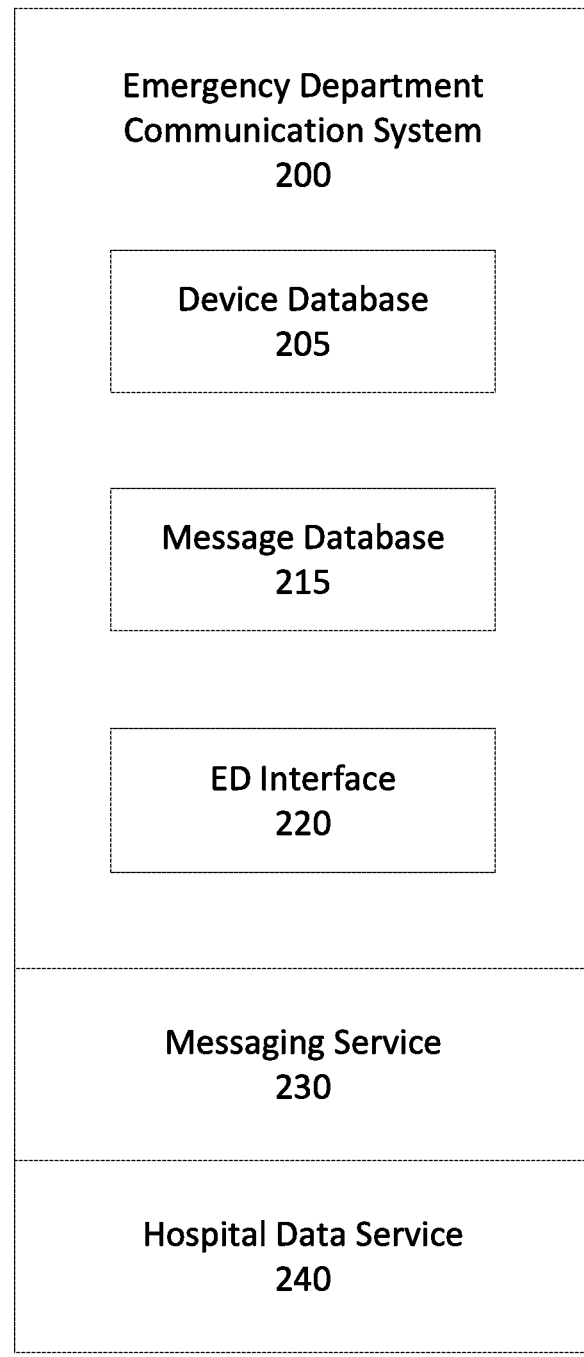
FIG. 2 is a conceptual block diagram illustrating an example emergency department communication system, in accordance with various embodiments of the subject technology.

FIG. 2 is a conceptual block diagram illustrating an example emergency department (ED) communication system 200, in accordance with various embodiments of the subject technology. The ED communication system 200 may include a device database 205, a message database 215, and an emergency department (ED) interface 220. In some embodiments, the ED communication system 200 may also include one or more messaging services 230 and one or more hospital data services 240. Although in other embodiments, the messaging services 230 and hospital interface services 240 may be external to the ED communication system 200. For example, the messaging services 230 and hospital interface services 240 may be provided by third-parties or hosted on a separate system.

The ED interface 220 is configured to provide an interface for emergency department (ED) devices to interact with and access the services provided by the emergency department communication system 200. For example, an ED device may access the services via an application interface provided by software installed on the ED device and/or a website via a web browser running on the ED device. Accordingly, the ED interface 220 may include, for example, one or more web servers, application servers, or other components configured to provide the communication services and interact with the ED device.

The device database 205 is configured to store information associated with devices that are registered or in the process of being registered with the ED communication system 200. For example, the device database may include an entry or record for each device registered with the ED communication system 200. For example, for patient devices, each entry or record may include one or more medical record numbers (MRNs) or other patient identifiers, contact information (e.g., a phone number, an application user name, an email address, or other device identifier), various timestamps for various steps in the process (e.g., starting registration, completing registration, etc.), or status information.

In some embodiments, the device database 205 may also store information for ED devices authorized to communicate with registered patient devices. Entries for ED devices may include device identifiers, user account information (e.g., user name/password combinations), user profile information (e.g., user name, role, etc.), or other information that may be used by the ED communication system 200.

The message database 215 is configured to store prepared communications for patients. The communications may include pre-written messages that include progress updates, notifications, information or links to bios of various members of the ED team, information or links to information about various health or medical information, etc. The messages may be associated with various metadata in the message data. For example, information or links to bios may be associated with an ED team member identifier. Progress updates or notifications may be associated with various ED events (e.g., heavy ambulance traffic, lab events, discharge events, patient transition events, etc.). According to some embodiments, the message database 215 may also store a record of message sent to patient devices and timestamps when they were sent to patient devices.

The emergency department (ED) interface 220 is configured to communicate with ED devices and provide ED devices with an interface with which to view the status of patient and patient devices registered with the ED communication system and allow ED devices to send patient devices communications. As is discussed in further detail below, the ED interface 220 may provide these features via a dashboard to ED devices. The dashboard may be provided by a web interface (e.g., a web server) of ED interface 220 such that the dashboard may be viewed in a web browser on the ED device. In other embodiments, the dashboard may be provided by an application interface (e.g., an application server) of ED interface 220 such that the dashboard may be viewed in an application or other software running on the ED device.

Once an ED team member generates a message or other communication to send to a particular patient device via the dashboard, the messaging service 230 is configured to transmit the message to the patient device. According to some embodiments, the messaging service 230 may transmit messages to patient devices using short message service (SMS) text messages over a cellular network. However, other means of transmitting messages may also be used. For example, communications may be sent via various messaging applications and audio or video messages may also be sent.

The hospital data service 240 may be configured to manage and provide various information about patients. The hospital data service 240 may be, for example, an electronic health record (EHR) service configured to store patient information and manage patient care through the care process. Although the hospital data service 240 and the ED communication system 200 are shown in FIG. 2 as distinct entities, in some embodiments, they may be integrated into a single unit.

Figure 3:
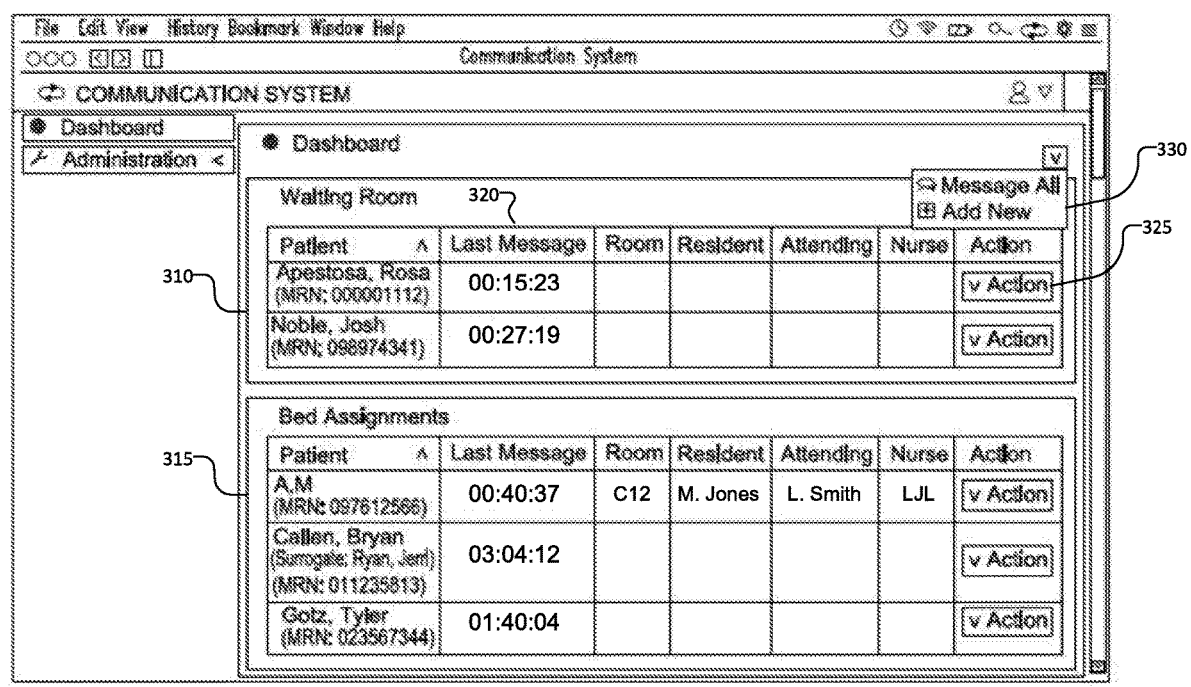
FIG. 3 is an illustration of a dashboard interface, in accordance with various embodiments of the subject technology.

FIG. 3 is an illustration of a dashboard interface 300, in accordance with various embodiments of the subject technology. The dashboard interface 300 may be provided by an emergency department communication system such as the emergency department communication system 200 shown in FIG. 2. The dashboard interface 300 is configured to be displayed on an ED device and enable ED team members to access and update patient information, select patients to interact with, transmit messages to patient devices, and perform any other features provided by the ED communication system.

The dashboard interface 300 shown in FIG. 3 is shown for illustrative purposes and other types of interfaces may be implemented in other embodiments. For example, the dashboard interface 300 in FIG. 3 is shown as a web interface that is loaded into a web browser running on an ED device. However, in other embodiments, the dashboard interface may be implemented as an application interface on software running on the ED device. In other embodiments, other types of interfaces (e.g., an audio interface provided by a digital voice assistant, augmented or virtual reality interface, etc.) may be used in combination or instead of a dashboard interface.

The dashboard interface 300 in FIG. 3 includes information about patients registered with the ED communication system and organizes the information in a clear and efficient manner. For example, the dashboard interface 300 shows an entry for each registered patient and the patient entries are grouped by patient status. In particular, there is an interface element 310 that groups together patients that are in the waiting room and an interface element 315 that groups together patients that are assigned to beds in the emergency room or the emergency department facilities. Additional groupings of patients that are not shown in the limited space in FIG. 3 may include registered patients that have been discharged, registered patients that have exited the facilities early, patients that have not yet registered, patients that are in the process of registering, or any other status that is tracked by the ED communication system.

Each patient entry may include information such as a patient name, a patient identifier such as a medical record number (MRN), a room, bed, or location that the patient has been assigned, and a resident, attending, and/or nurse that is assigned to the patient. Each patient entry may also include message information for the patient such as a field 320 specifying a timestamp for the last message that the patient received or information about patient authorized individuals (e.g., surrogates) that may receive messages on the patient's behalf.

In some cases, it is important to send regular updates to patients or patient authorized individuals. This is important to keep individuals informed, improve patient contentment, and reduce any dissatisfaction or related issues. For example, the ED team may determine that it is desirable to send a message or update to patients or patient authorized individuals at least once every 15 minutes, 30 minutes, 45 minutes, 60 minutes, 75 minutes, 90 minutes, 105 minutes, 120 minutes, 135 minutes, 150 minutes, 165 minutes, 3 hours, or other time interval. The desired time interval may be for all patient statuses or based on the current status of a patient (e.g., whether the patient is in the waiting room, assigned to a bed, room, or other location, or other status).

According to some embodiments, the ED communication system may help ED team members send regular updates to patients or patient authorized individuals. For example, the ED communication may use timestamp for the last message that the patient received in order to highlight (visually or otherwise) patient entries in the dashboard interface 300. The patient entries may be, for example, color coded based on how long it has been since the registered device associated with a patient entry last received a message.

For example, patient entries whose timestamp for the last message is within a certain time threshold of the current time may not be highlighted or be highlighted with a particular color while patient entries whose timestamp for the last message is beyond the time threshold of the current time may be highlighted a different color. Furthermore, multiple time thresholds or time periods may be used. For example, if the time elapsed since the last message is between half an hour and an hour, the patient entry may be highlighted a certain color. If the time elapsed since the last message is between an hour and 2 hours, the patient entry may be highlighted another color. If the time elapsed since the last message is between 2 hours and 4 hours, the patient entry may be highlighted using still another color. Additional time periods may be associated with further colors indicating the amount of time that has elapsed since a message has been sent for the patient entry. The thresholds and/or time periods may be provided by default by the ED communication system or specified by an administrator or ED team member. Furthermore, the thresholds and/or time periods may be specified for all patient statuses, specific patient statuses, or specific patients.

Each patient entry may also be associated with an action interface element 325 that enables an ED team member to perform various actions with respect to the patient. For example, an ED team member may select the action interface element 325 for a patient to and view options to message the patient or patient authorized individual, transition the patient to a different status (e.g., assigning a patient from the waiting room to a bed), or view more details associated with the patient. According to some embodiments, the information about a patient that is displayed with the more details option or in the patient entry may be retrieved from a hospital data service such as an electronic health record (EHR) service using a patient's MRN.

Each grouping of patients may also have an action interface element that enables an ED team member to perform various actions with respect to all or multiple patients in the patient group. For example, an ED team member may select the action interface element and view a menu of options 330 for the patient group. As shown in FIG. 3, the menu of options 330 for the patient group may include messaging all patients in the patient group or adding a new patient to the patient group.

In one example process flow, an ED team member may register a new patient or patient authorized device to the ED communication system by selecting the "Add New" option in the menu of options 330 for the waiting room group of patients. In response to the selection, the ED communication system may provide an interface and process flow for the ED team member to register a new patient or patient authorized device.

Figure 4:
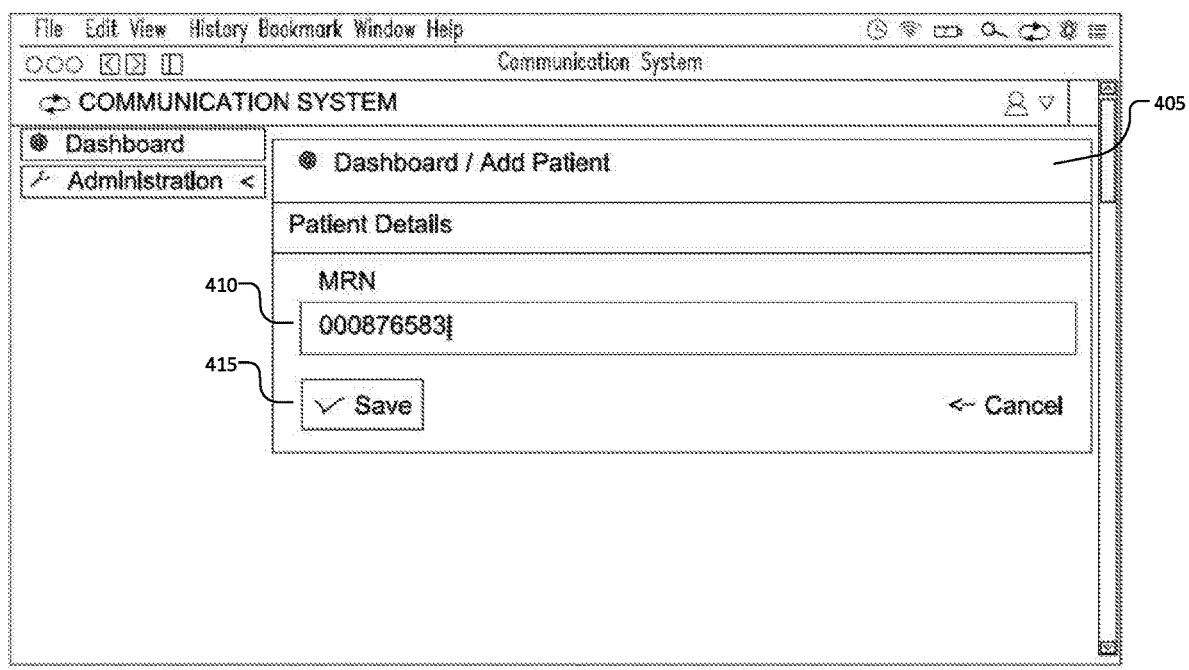
FIG. 4 and FIG. 5 are illustrations dashboard interfaces for registering a patient authorized device to the emergency department communication system, in accordance with various embodiments of the subject technology.
Figure 5:
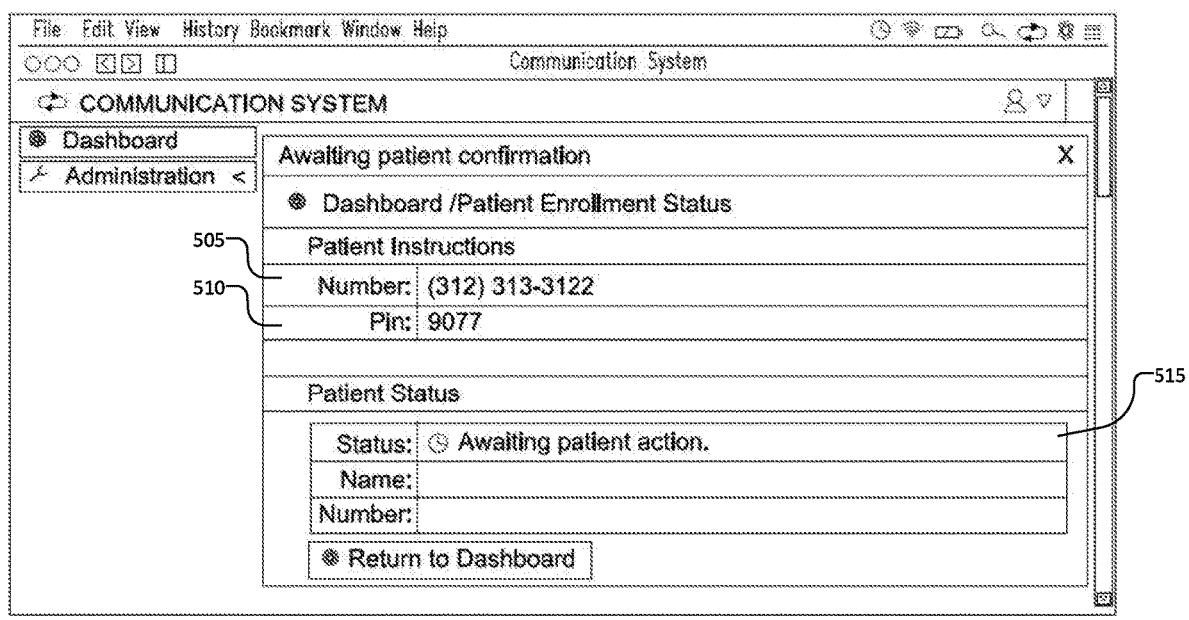

For example, FIG. 4 and FIG. 5 are illustrations dashboard interfaces for registering a patient authorized device to the emergency department communication system, in accordance with various embodiments of the subject technology. The dashboard interface 400 of FIG. 4 may be displayed in response to an ED team member selecting the option to register a new patient authorized device. The dashboard interface 400 may include an interface element 405 where the ED team member may enter registration information for the patient or patient authorized device. In the embodiment shown in FIG. 4, the registration information may include a medical record number (MRN) or other patient identifier, which may be input into input field 410 by the ED team member and submitted to the ED communication system by selecting the "Save" interface element 415.

The ED communication system may receive the registration information from the ED device and store the registration information (e.g., the MRN) in an entry in the patient database. The ED communication system may also generate a unique identifier and transmit the unique identifier back to the ED device for display in a dashboard interface. For example, the dashboard interface 500 of FIG. 5 may include a field 510 for the display of the unique identifier (e.g., a PIN number). The dashboard interface 500 may also include additional registration information such as a phone number 505 that is associated with the registration process and a registration status 515. The phone number 505 may be a phone number associated with the ED communication system for the emergency department or one of many phone numbers that is selected for the patient device by the ED communication system. The unique identifier and/or the phone number may be read by the ED team member and given to a patient or patient authorized team member to continue the process.

According to some embodiments, the patient or the patient's surrogate may sign a consent form provided by the ED team. The consent form may provide the ED team with patient consent to send emergency department communications to a patient authorized device via the ED communication system. After consent is given, the ED team member may provide the phone number 505 and unique identifier 510 shown on dashboard interface 500 to the patient or the patient's surrogate to continue with the registration process. The patient or the patient's surrogate may be instructed to send a SMS text message including the unique identifier 510 to the phone number 505.

Figure 6:
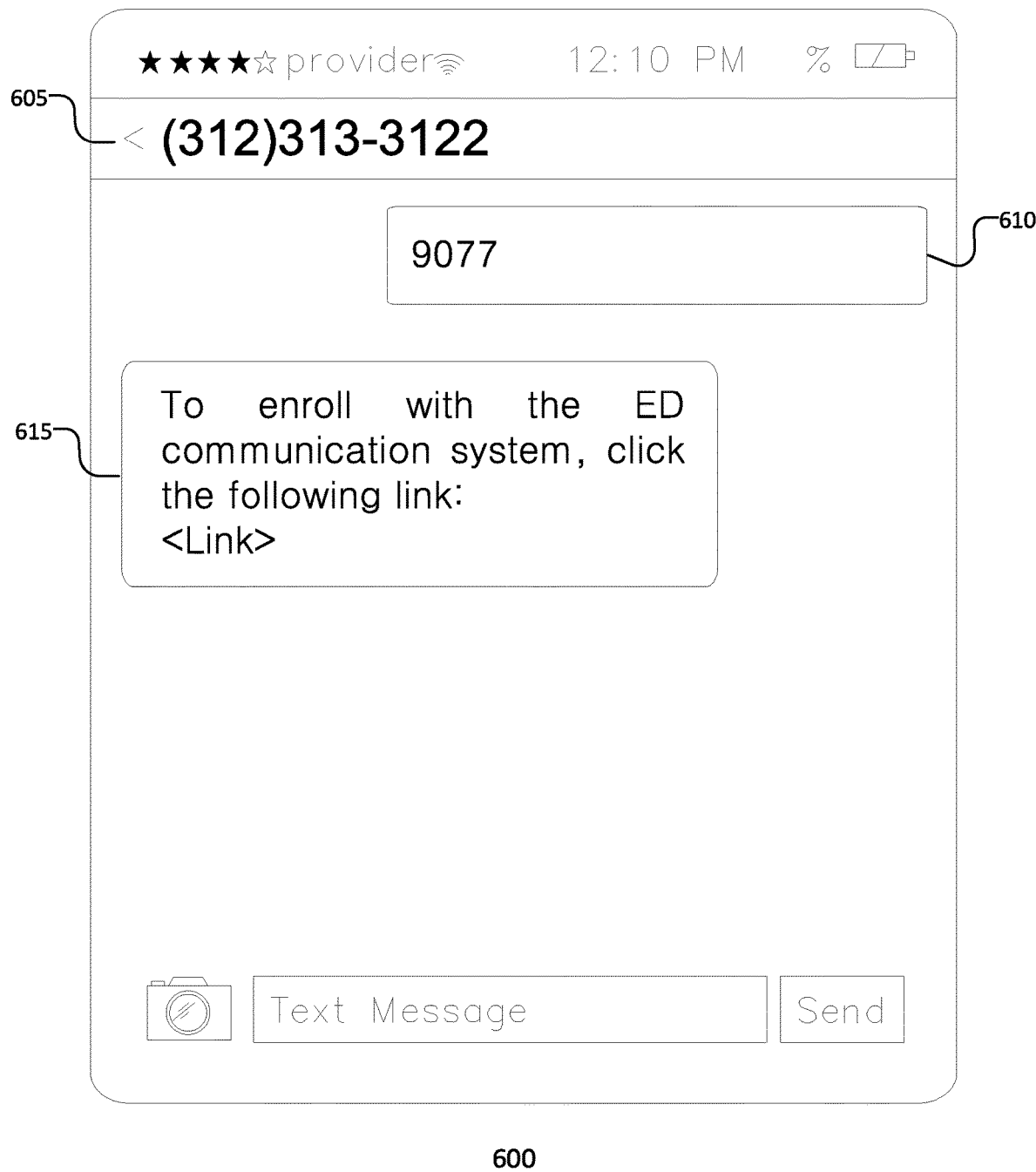
FIG. 6 is an illustration of a communication interface on a patient device, in accordance with various embodiments of the subject technology.

FIG. 6 is an illustration of a communication interface 600 on a patient device, in accordance with various embodiments of the subject technology. In FIG. 6, the communication interface 600 is in the form of an SMS text messaging interface. However, in other embodiments, other types of interfaces may also be used. After receiving the instructions from the ED team member, the patient or the patient's surrogate may use the patient device to send a text communication 610 including the unique identifier to the provided phone number 605.

The ED communication system may receive the communication 610 from the patient device via the messaging service. The unique identifier in the communication 610 allows the ED communication system to determine which entry in the patient database that the received communication is associated with and store the contact information associated with the communication in the entry. In the example scenario illustrated in FIG. 6, the contact information is the phone number that sent the text communication 610. However, as discussed, the communication means and contact information may be in other forms such as an application user name, an email address, or other device identifier.

In response to receiving the communication 610, the ED communication system may also respond to the patient or patient's surrogate by sending a follow-up communication 615 to the patient device that includes a link for the patient or the patient's surrogate to complete registration. The patient or patient's surrogate may select the link on the patient device and be taken to a website hosted by a webserver. The website may include additional consent notices and request additional patient information and consent approvals. For example, the website may include prompts that request the patient first and last name and/or the first and last name of a patient authorized surrogate that the patient consents to receive the patient's communications. The patient or patient's surrogate may confirm consent to the consent terms and submit the additional patient information and consent approval to the ED communication system via the website.

The ED communication system may receive the consent approval and additional patient information, store the consent approval and additional patient information in the patient database, and complete registration of the patient device. Once the registration of the patient device is completed, an entry for the patient device may appear in the dashboard. For example, referring back to the dashboard interface 300 of FIG. 3, a new entry for the newly registered patient device may appear in interface element 310 that groups together patients that are in the waiting room. An initial welcome communication may also be automatically sent to the patient device upon completion of registration. The initial welcome communication may notify the patient or the patient's surrogate of successful registration.

Figure 7:
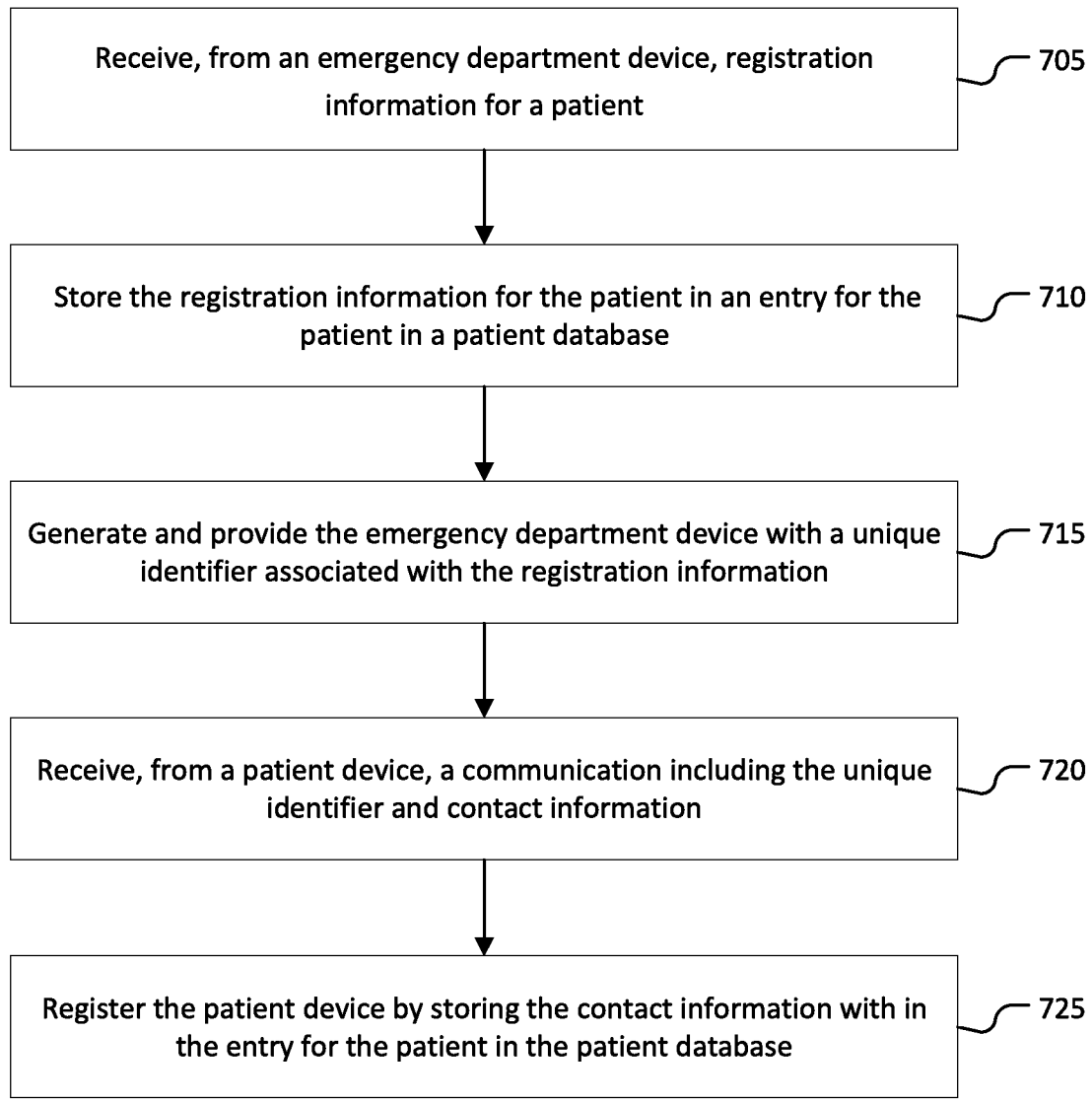
FIG. 7 shows an example method for communicating with a patient device in an emergency department environment, in accordance with various embodiments of the subject technology.

FIG. 7 shows an example method for communicating with a patient device in an emergency department environment, in accordance with various embodiments of the subject technology. Although the methods and processes described herein may be shown with certain steps and operations in a particular order, additional, fewer, or alternative steps and operations performed in similar or alternative orders, or in parallel, are within the scope of various embodiments unless otherwise stated. The method 700 may be implemented by a system such as, for example, the ED communication system 120 of FIG. 1.

At operation 705, the system may receive, from an emergency department device, registration information for a patient device. The registration information may include, for example a medical record number (MRN), a patient name, other patient identifier, or patient information. In some embodiments, registration information may be limited to the MRN or other assigned identifier in order to reduce the risk of privacy violations and increase the security of the messaging system.

The system may store the registration information for the patient device in an entry for the patient device in a patient database at operation 710. At operation 715, the system may generate a unique identifier associated with the registration information and provide the unique identifier to the ED device. In some embodiments, the unique identifier may be a personal identification number (PIN) that an ED team member can provide to a patient or patient's surrogate in order to continue the registration process of the patient device.

The patient or patient's surrogate can use include the unique identifier generated by the system in a communication (e.g., a text message) sent from the patient device to the system. At operation 720, the system receives the communication, which also includes contact information (e.g., a phone number of the sending device) for the patient device. The system identifies the entry for the patient device in the patient database based on the unique identifier included in the communication and, at operation 725, completes the registration process for the patient device by storing the contact information with in the entry for the patient in the patient database.

As discussed above, once the registration of the patient device is completed, an entry for the patient device may appear in the dashboard. For example, referring back to the dashboard interface 300 of FIG. 3, a new entry for the newly registered patient device may appear in interface element 310 that groups together patients that are in the waiting room. An ED team member may select an entry associated with a patient to perform various actions with respect to the patient. For example, an ED team member may select the action interface element 325 for a patient to and view options to message the patient or patient authorized individual, transition the patient to a different status, or view more details associated with the patient. Similarly, actions may also be taken for patients associated with other statuses.

In one illustrative example, the ED team member may select the action interface element 325 to view a menu of actions associated with patient Rosa Apestosa. One of the actions may be to change the status of the patient from one status to another. Upon selection of the action to change the status of the patient, the ED communication system may provide a dashboard interface for display on the ED device that enables the ED team member to transition the patient.

Figure 8:
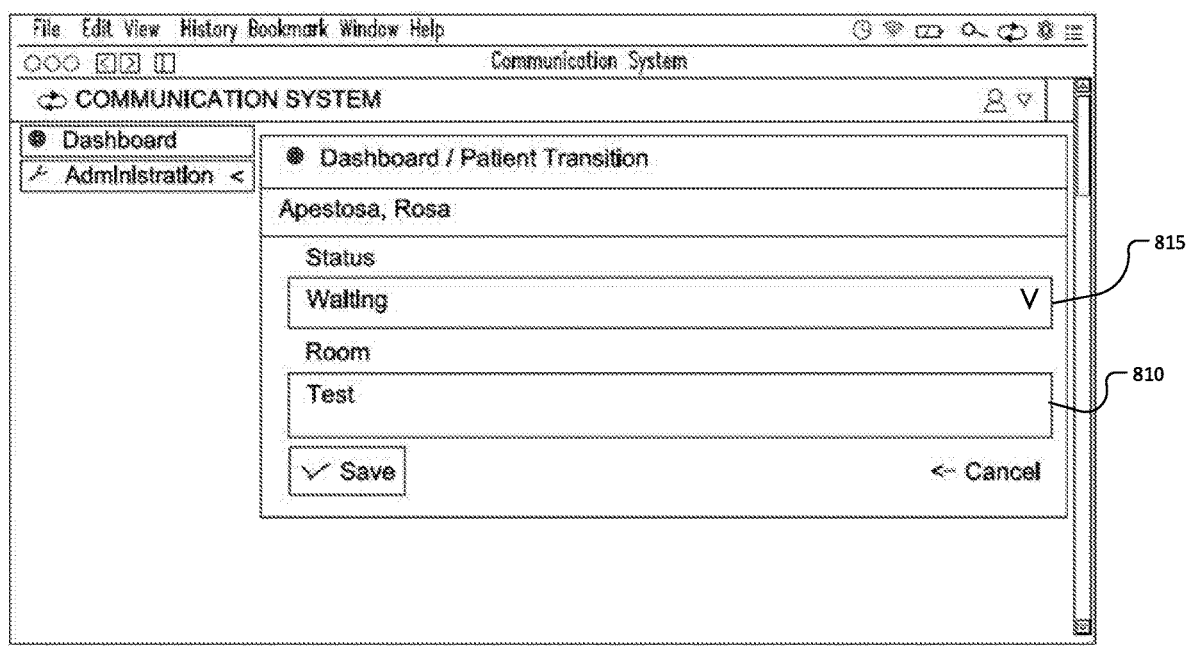
FIG. 8 is an illustration of a dashboard interface for transitioning a patient from one status to another status, in accordance with various embodiments of the subject technology.

FIG. 8 is an illustration of a dashboard interface 800 for transitioning a patient from one status to another status, in accordance with various embodiments of the subject technology. The dashboard interface 800 includes a status field 805 where the ED team member may view the current status of the selected user and make changes to the status (e.g., via the dropdown menu). For example, the status may be changed from a "waiting" status to an admitted status where the patient has been assigned a bed or room. The ED team member may further specify the location assigned to the patient in field 810 or other information related to the patient such as a reason for visiting or requesting assistance. As discussed above, additional statuses may include, but are not limited to, patients that have exited the facilities early, patients that have not yet registered, patients that are in the process of registering, or any other status that is tracked by the ED communication system.

As discussed above, the ED team member may also select an option to send a registered device associated with a patient a message. Upon selection of the option to transmit a message to a registered device for a patient, the ED communication system may provide a dashboard interface for display on the ED device that enables the transmission of the message to send to the registered device. In various embodiments, the ED team member may craft a message to send, select a pre-written message from a message database, and/or customize a pre-written message or message template to send.

Figure 9:
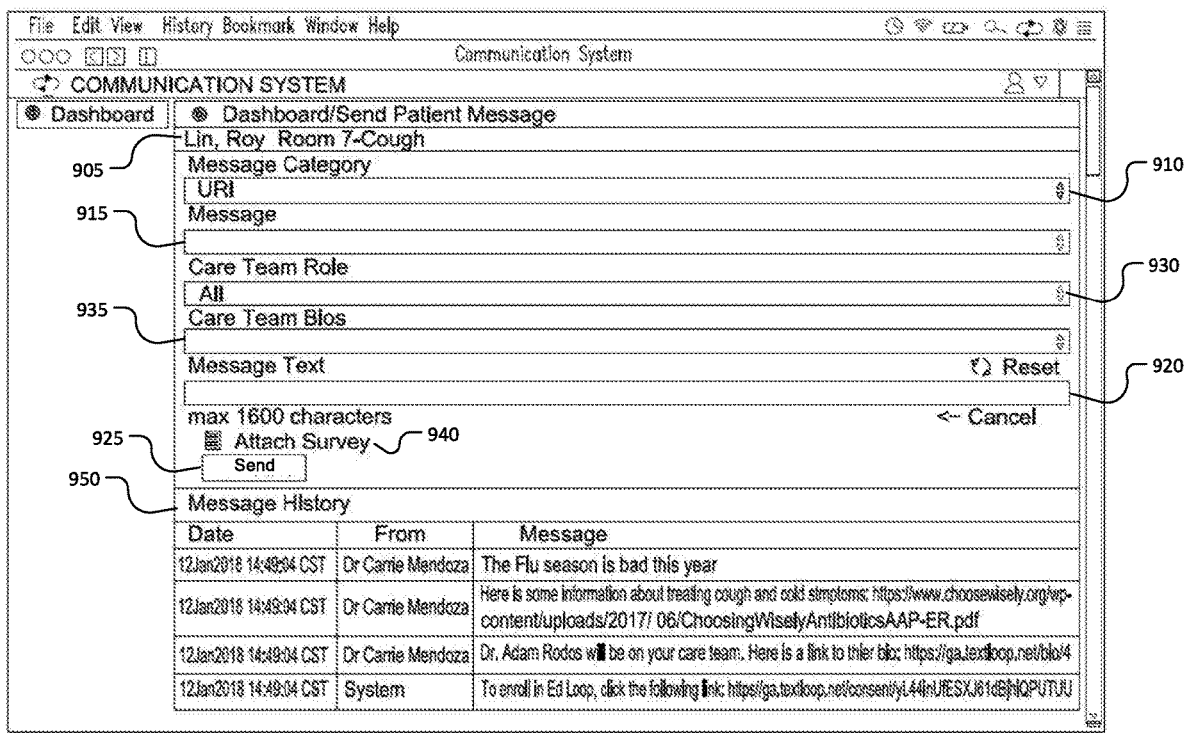
FIGS. 9 and 10 are illustrations of a dashboard interface for sending a communication to a registered device, in accordance with various embodiments of the subject technology.

For example, FIG. 9 is an illustration of a dashboard interface 900 for sending a communication to a registered device, in accordance with various embodiments of the subject technology. The dashboard interface 900 may include information about the patient that the ED team member selected to send a message. The information 905 may include, for example, a patient name, a location (e.g., an assigned room or bed), a reason for seeking assistance, an initial diagnosis or diagnosis category, etc.

In some cases, the number of pre-written messages and/or message templates may be quite large. Accordingly, these pre-written messages and message templates may be stored in a message database (e.g., message database 215 of FIG. 2) along with metadata that may be used to categorize and organize messages and message templates. The metadata that may be associated with various pre-written messages and message templates may include, for example, a message category, care team roles, care team members, message previews or titles, etc. An ED team member may use this metadata to more efficiently filter and/or select pre-written messages and message templates.

Figure 10:
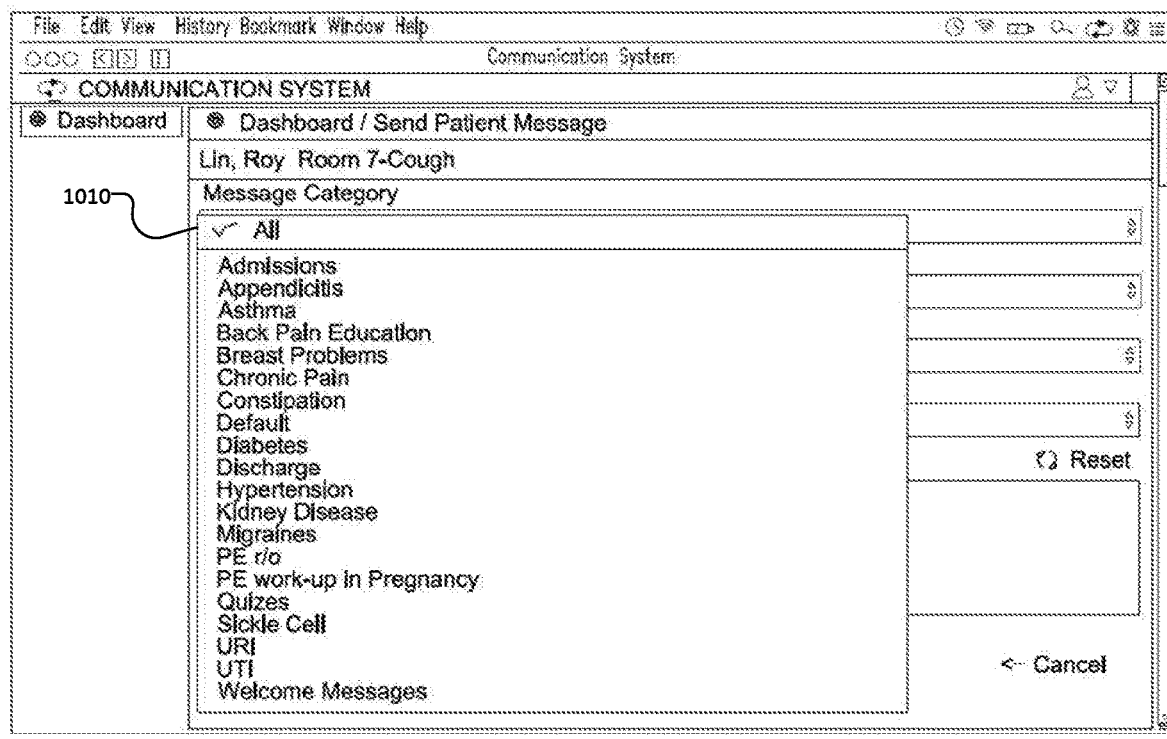

For example, the dashboard interface 900 in FIG. 9 includes a message category field 910 that an ED team member may use to filter pre-written messages or message templates. FIG. 10 shows the dashboard interface 1000 where the ED team member may use the dropdown menu 1010 for the message category field to select a message category. Returning to FIG. 9, the dashboard interface 900 shows that the "URI" or "upper repertory infection" message category has been selected in the message category field 910. Accordingly, the ED communication may filter the available messages or message templates based on the selected message category of "URI" and provide only those messages or message templates that belong in the "URI" message category.

The ED team member may then select from the filtered set of messages or message templates that belong in the "URI" message category using the message field 915. The titles or message previews of the filtered set of messages or message templates may be displayed in message field 915 in order to provide some guidance to ED team members on which message or message template is to be selected while also saving some space in the message selection interface. The full contents of the selected message may be provided in message content field 920. Furthermore, the ED team member may also make changes or customizations to the message in message content field 920 before sending the message using interface element 925.

The dashboard interface 900 may also enable the ED team member to send a pre-written biography or bio for one or more ED team members (or care team members) that will be attending to the patient. The bio may be sent by itself or appended to any message or message template for delivery to the patient device. However, when there are a large number of ED team members, it may be difficult and time consuming to identify and select an appropriate bio. The dashboard interface 900 may aid in the selection of an appropriate bio by storing, in the message database, an association of the pre-written bios with a care team role in addition to a care team name or other identifier. For example, the care team role (e.g., nurse, attending, physician, etc.) may be selected in the care team role field 930. The care team bios may be filtered in the care team bio field 935 based on the selected care team role in field 930.

According to some embodiments, a survey or link to a survey hosted by a web server may also be sent or attached to any message for delivery using the attach survey feature 940. The survey provided may enable patients to give feedback and for patient satisfaction scores to be calculated based on the patient feedback. As discussed above, patient satisfaction scores may have a direct impact on hospital revenue, compliance, and compensation for doctors or other emergency department team members.

The ED communication system may provide for a more effective and convenient means to obtain patient feedback, thereby increasing participation and accuracy. For example, an ED team member may attach the survey or survey link to any message by using the attach survey feature 940. In some embodiments, the ED communication system may also automatically transmit the survey or survey link when a patient entry transitions to a particular status (e.g., the patient is discharged). The patient may fill out the survey and submit the results (e.g., through a web interface) back to the ED system where they can be stored and used to calculate patient satisfaction scores or other measures.

Once the ED team member is finished composing the message, the message may be sent to the patient device by selecting interface element 925. According to some embodiments, selecting interface element 925 may activate one or more message translation features. For example, selecting interface element 925 may cause a language dropdown menu to appear. The ED team member may select a language for translation. In response, the ED communication system may translate and send the message.

After the message is sent by the ED communication system, a record of the communication may be stored and used to provide a message history on the dashboard interface. For example, the dashboard interface 900 of FIG. 9 includes a message history 950 of messages sent to the registered patient device by the system. The message history 950 may include a timestamp for when the message was sent, a sender identifier, and the message that was sent. The message history 950 may also show both the original message as well as the translated message.

Figure 11:
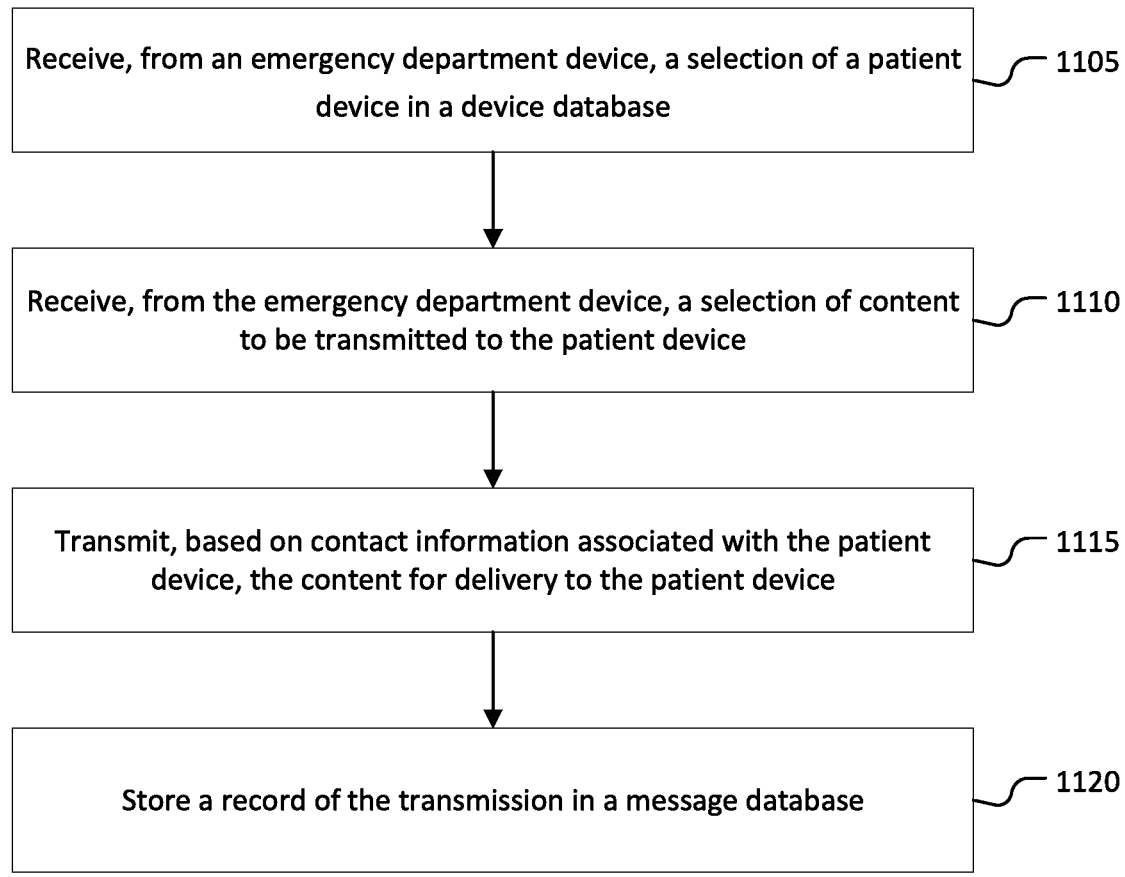
FIG. 11 shows an example method for sending a communication to a registered device, in accordance with various embodiments of the subject technology.

FIG. 11 shows an example method 1100 for sending a communication to a registered device, in accordance with various embodiments of the subject technology. Although the methods and processes described herein may be shown with certain steps and operations in a particular order, additional, fewer, or alternative steps and operations performed in similar or alternative orders, or in parallel, are within the scope of various embodiments unless otherwise stated. The method 1100 may be implemented by a system such as, for example, the ED communication system 120 of FIG. 1.

At operation 1105, the system may receive, from an emergency department device, a selection of a registered patient device. Information, such as contact information, for the registered patient device may be stored in a record or entry in a device database. For example, an ED team member may use the dashboard interface 300 of FIG. 3 to select a patient to send a message to. The dashboard interface 300 may include a number of entries for patients that are associated with a registered patient device (e.g., the patient's device or the device of a patient authorized individual). Each entry in the dashboard interface 300 may be associated with one or more patient devices that have been registered with the system and have a corresponding entry in the device database.

As discussed above, the entries may be color coded based on the time that has elapsed since the last time the patient device associated with the entry received a message from an ED team member and/or the system. For example, for each entry in the dashboard interface 300, the system may identify, using the message database, the timestamp for the last message received by the patient device associated with the entry. The system may compare the timestamp for the last message with the current time, select a highlighting scheme or color code for the entry based on the difference between the timestamp for the last message and the current time, and display the entry in the dashboard interface 300 using the selected highlighting scheme or color code. The highlighting of the patient entries in the dashboard interface 300 may help ED team members determine who should be selected to send a message to.

In response to the selection of the patient and corresponding patient device, the system may provide an interface for the ED team member to create and/or select content to be transmitted to the selected patient device. For example, the system may provide for the display of dashboard interface 900 of FIG. 9 on the ED device.

At operation 1110, the system may receive, from the emergency department device, a selection of content to be transmitted to the patient device. For example, using dashboard interface 900 of FIG. 9, the ED team member may create a message, use a pre-written message or message template, and/or update any message to send to the patient device and send the selected content to the system using interface element 925.

The selected content may be received by the system and any number of processing operations may be performed on the selected content. The processing operations may include, for example, formatting the content for delivery, checking the message for personally identifiable information or other information that may violate HIPAA or other regulations, inserting content (e.g., images, illustrations, video, audio, biographies, etc.) referenced by the content selected by the ED team member.

At operation 1115, the system transmits the content for delivery to the patient device based on contact information associated with the patient device that is stored in the device database. In some embodiments, one or more messaging services may be used to transmit the content either directly or indirectly. For example, the messaging services may include an SMS messaging service.

At operation 1120, the system stores a record of the transmission in a message database. The records of the transmissions to the patient device may be used to provide information to various team members. For example, a message history 950 may be displayed in dashboard interface 900 of FIG. 9.

Figure 12:
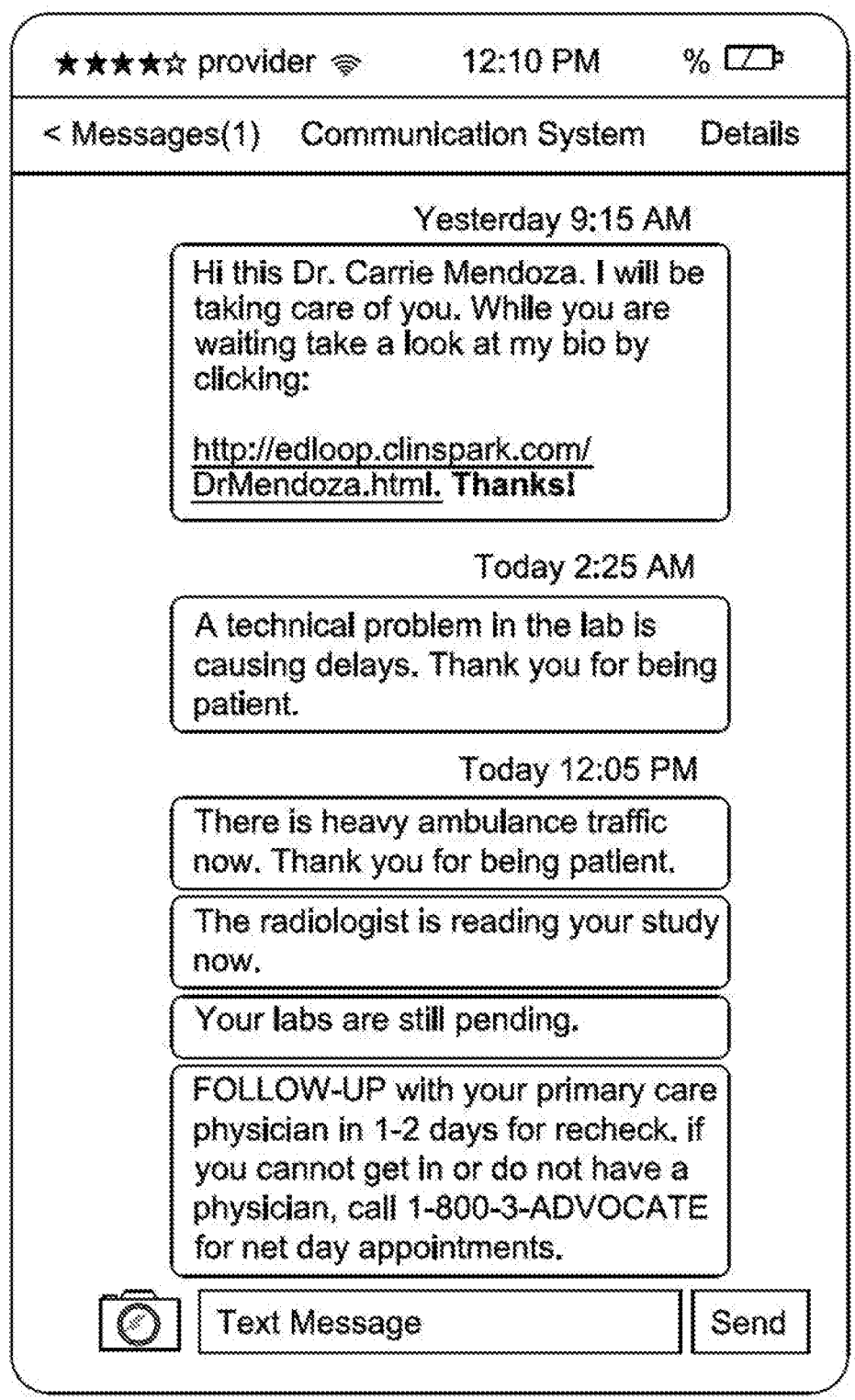
FIG. 12 is an illustration of an interface on a registered device that displays communications received from an emergency department communication system, in accordance with various embodiments of the subject technology.

FIG. 12 is an illustration of an interface 1200 on a registered patient device that displays communications received from an emergency department communication system, in accordance with various embodiments of the subject technology. The communications may be displayed in a messaging interface, such as an SMS messaging interface or other communication interface. The communications may include, for example, introductory messages or greetings, biographies, links to various content, notifications about department events, delays, or other issues, updates on a patient's status, follow up information, or any other information that an ED team member may wish to communicate with a patient or patient authorized individual.

Figure 13A:
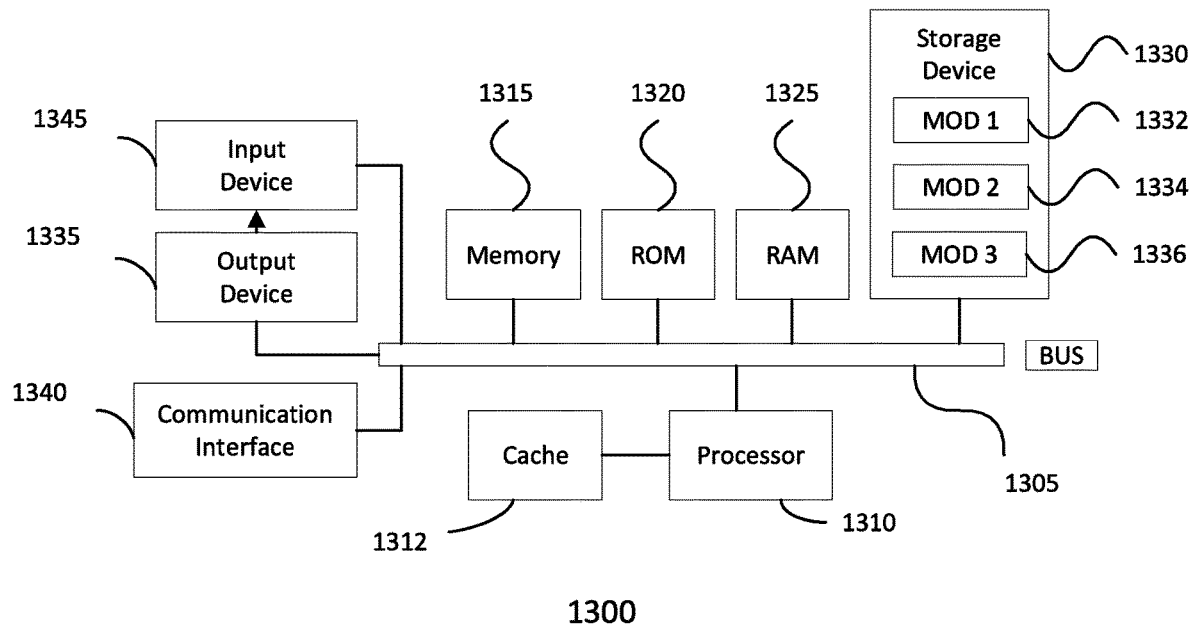
FIG. 13A and FIG. 13B show example possible system embodiments.
Figure 13B:
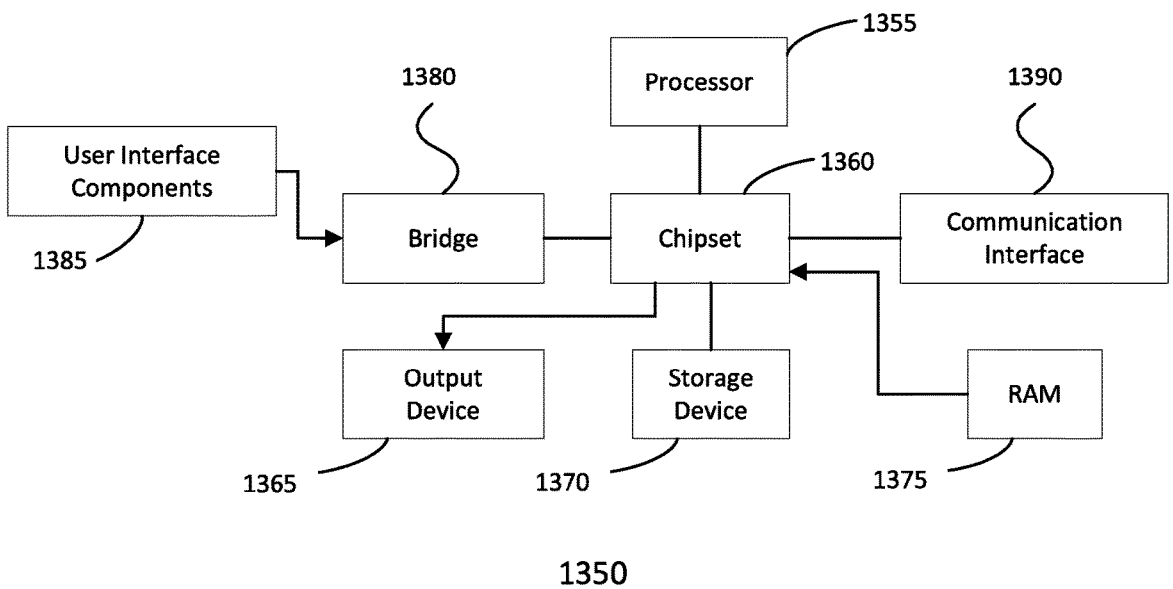

FIG. 13A and FIG. 13B show example possible system embodiments. The more appropriate embodiment will be apparent to those of ordinary skill in the art when practicing the present technology. Persons of ordinary skill in the art will also readily appreciate that other system embodiments are possible.

FIG. 13A shows a conventional system bus computing system architecture 1300 wherein the components of the system are in electrical communication with each other using a bus 1305. Example system 1300 includes a processing unit (CPU or processor) 1310 and a system bus 1305 that couples various system components including the system memory 1315, such as read only memory (ROM) 1320 and random access memory (RAM) 1325, to the processor 1310. The system 1300 can include a cache of high-speed memory connected directly with, in close proximity to, or integrated as part of the processor 1310. The system 1300 can copy data from the memory 1315 and/or the storage device 1330 to the cache 1312 for quick access by the processor 1310. In this way, the cache can provide a performance boost that avoids processor 1310 delays while waiting for data. These and other modules can control or be configured to control the processor 1310 to perform various actions. Other system memory 1315 may be available for use as well. The memory 1315 can include multiple different types of memory with different performance characteristics. The processor 1310 can include any general purpose processor and a hardware module or software module, such as module 1 1332, module 2 1334, and module 3 1336 stored in storage device 1330, configured to control the processor 1310 as well as a special-purpose processor where software instructions are incorporated into the actual processor design. The processor 1310 may essentially be a completely self-contained computing system, containing multiple cores or processors, a bus, memory controller, cache, etc. A multi-core processor may be symmetric or asymmetric.

To enable user interaction with the computing device 1300, an input device 1345 can represent any number of input mechanisms, such as a microphone for speech, a touch-sensitive screen for gesture or graphical input, keyboard, mouse, motion input, speech and so forth. An output device 1335 can also be one or more of a number of output mechanisms known to those of skill in the art. In some instances, multimodal systems can enable a user to provide multiple types of input to communicate with the computing device 1300. The communications interface 1340 can generally govern and manage the user input and system output. There is no restriction on operating on any particular hardware arrangement and therefore the basic features here may easily be substituted for improved hardware or firmware arrangements as they are developed.

Storage device 1330 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 1325, read only memory (ROM) 1320, and hybrids thereof.

The storage device 1330 can include software modules 1332, 1334, 1336 for controlling the processor 1310. Other hardware or software modules are contemplated. The storage device 1330 can be connected to the system bus 1305. In one aspect, a hardware module that performs a particular function can include the software component stored in a computer-readable medium in connection with the necessary hardware components, such as the processor 1310, bus 1305, display 1335, and so forth, to carry out the function.

FIG. 13B shows a computer system 1350 having a chipset architecture that can be used in executing the described method and generating and displaying a graphical user interface (GUI). Computer system 1350 is an example of computer hardware, software, and firmware that can be used to implement the disclosed technology. System 1350 can include a processor 1355, representative of any number of physically and/or logically distinct resources capable of executing software, firmware, and hardware configured to perform identified computations. Processor 1355 can communicate with a chipset 1360 that can control input to and output from processor 1355. In this example, chipset 1360 outputs information to output 1365, such as a display, and can read and write information to storage device 1370, which can include magnetic media, and solid state media, for example. Chipset 1360 can also read data from and write data to RAM 1375. A bridge 1380 for interfacing with a variety of user interface components 1385 can be provided for interfacing with chipset 1360. Such user interface components 1385 can include a keyboard, a microphone, touch detection and processing circuitry, a pointing device, such as a mouse, and so on. In general, inputs to system 1350 can come from any of a variety of sources, machine generated and/or human generated.

Chipset 1360 can also interface with one or more communication interfaces 1390 that can have different physical interfaces. Such communication interfaces can include interfaces for wired and wireless local area networks, for broadband wireless networks, as well as personal area networks. Some applications of the methods for generating, displaying, and using the GUI disclosed herein can include receiving ordered datasets over the physical interface or be generated by the machine itself by processor 1355 analyzing data stored in storage 1370 or 1375. Further, the machine can receive inputs from a user via user interface components 1385 and execute appropriate functions, such as browsing functions by interpreting these inputs using processor 1355.

It can be appreciated that example systems 1300 and 1350 can have more than one processor or be part of a group or cluster of computing devices networked together to provide greater processing capability. The processor may include a central processing unit (CPU), a graphic processing unit (GPU), other processing units, or a combination thereof.

For clarity of explanation, in some instances the present technology may be presented as including individual functional blocks including functional blocks comprising devices, device components, steps or routines in a method embodied in software, or combinations of hardware and software.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims.

What is claimed is:

1. A computer-implemented method for a secure communication system comprising:
   providing a device database that is configured to store information associated with one or more internal network devices or one or more extort al network devices;
   providing a message database that is configured to store prepared communications for external users or to record communications to external users;
   providing an internal network interface that is configured to communicate with the one or more internal network devices and to provide a dashboard interface to the one or more internal network devices;
   providing a messaging service that is configured to handle communications between the secure communication system and the one or more internal network devices or the one or more external network devices;
   providing an external user data service configured to store or obtain external user information;
   receiving, from at least one of the one or more internal network devices via the dashboard interface, registration in for a new external user device;
   storing the registration information for the external user device in an entry for the new external user device in the device database;
   generating a unique identifier associated with the registration information for the new external user device;
   providing the unique identifier to the internal network device via the dashboard interface;
   receiving, from the new external network device via the messaging service, a communication including the unique identifier and contact information;

identifying the entry for the external user from a plurality of entries in the device database based on the unique identifier;

enabling, based on the identifying, communications between one or more internal network devices to the new external network device by storing the contact information in the entry for the new external device in the device database;

determining groupings of the one or more external network devices based on external user location, external user need for assistance, registered external users that have received assistance, external users that have not yet registered, or external users that are in the process of registering; and sending via the dashboard interface to at least one of the one or more internal network devices information describing one or more groupings of the one or more external network devices, wherein the dashboard interface is capable of receiving from at least one of the one or more internal network devices a selection of at least one of the one or mi re groupings of the one or more external network devices.

2. The computer-implemented method of claim 1, further comprising:

sending, based on the contact information, a consent request communication from the message database to the new external user device via the messaging service; and receiving, from the new external user device, a consent approval to the consent request communication via the messaging service; and storing the consent approval via the external user data service.

3. The computer-implemented method of claim 2, further comprising only enabling communications between one or more internal network devices to the new external network device if the consent approval associated with the new external network device is available via the external user data service.

4. The computer-implemented method of claim 2, wherein the consent request communication comprises a link to a webpage requesting consent, and wherein the consent approval is received from the new external network device through the messaging service via a web server hosting the webpage.

5. The computer-implemented method of claim 1, further comprising transmitting, based on the contact information, an initial communication indicating successful registration to the new external user device.

6. The computer-implemented method of claim 1, further comprising:

receiving, from at least one of the one or more internal network devices, a selection of an entry associated with at least one of the one or more external network devices and a selection of content to be transmitted to the at least one of the one or more external network devices; and transmitting the content for delivery to at least one of the one or more external network devices via the messaging service.

7. The computer-implemented method of claim 6, wherein the transmitting of the content for delivery to the at least one of the one or more external network devices comprises transmitting the content from the message database.

8. The computer-implemented of claim 1, wherein the registration information for the new external network device is a medical record number (MRN) for a patient associated with the new external network device.

9. The computer-implemented method of claim 8, further comprising:

retrieving, based on the MRN for the patient associated with the new external network device, patient information from the external user data service; and storing the patient information in the entry for the new external network device in the device database.

10. The computer-implemented method of claim 1, wherein the contact information is a phone number where the new external network device can receive communications.

11. The computer-implemented method of claim 1, further comprising:

determining a time elapsed since a last message was transmitted to the new external user device corresponding to the entry for the new external user device; and providing for a highlighting of the entry for the new external user device in a dashboard interface based on the time elapsed.

12. A system for a secure communication system comprising:

one or more processors; and at least one non-transitory computer-readable storage medium having stored therein instructions which, when executed by the one Or more processors, cause the system to provide:

a device database that is configured to store information associated with one or more internal user devices or one or more external user devices;

a message database that is configured to store prepared communications for external users or to record communications to external users;

an internal user interface that is configured to communicate with the one or more internal network devices and to provide a dashboard interface to the one or more internal network devices;

a messaging service that is configured to handle communications between the secure communication system and the one or more internal network devices or the one or more external user devices; and an external user data service configured to store or obtain external user information; and wherein the system is further configured to:

receive, from at least one of the one or more internal user devices via the dashboard interface, registration information for a new external user device;

store the registration information for the new external user device in an entry for the new external user device in the device database;

generate a unique identifier associated with the registration information for the new external user device;

provide the unique identifier to the internal user device via the dashboard interface;

receive, from the new external user device via the messaging service, a communication including the unique identifier and contact information;

identify the entry for the external user from a plurality of entries in the device database based on the unique identifier;

enable, based on the identifying, communications between one or more internal user devices to the new external user device by storing the contact information in the entry for the new external user device in the device database;

determine groupings of the one or more external network devices based on external user location, external user need for assistance registered external users that have received assistance, external users that have not yet registered, or external users that are in the process of registering; and send via the dashboard interface to at least one of the one or more internal network devices information describing one or more groupings of the one or more external network devices, wherein the dashboard interface is capable of receiving from at least one of the one or more internal network devices a selection of at least one of the one or more groupings of the one or more external network devices.

13. The system of claim 12, wherein the at least one non-transitory computer-readable storage medium stores instructions which, when executed by the one or more processors, cause the system to:

send, based on the contact information, a consent request communication from the message database to the new external user device via the messaging service; and receive, from the new external user device, a consent approval to the consent request communication via the messaging service; and store the consent approval via the external user data service.

14. The system of claim 13, wherein the system is further configured to only enable communications between one or amore internal user devices to the new external user device if the consent approval associated with the new external user device is available via the external user data service.

15. The system of claim 13, wherein the consent request communication comprises a link to a webpage requesting consent, and wherein the consent approval is received from the new external user device through the messaging service via a web server hosting the webpage.

16. The system of claim 12, wherein the at least one non-transitory computer-readable storage medium stores instructions which, when executed by the one or more processors, cause the system to:

transmit, based on the contact information, an initial communication indicating successful registration to the new external user device.

17. The system of claim 12, wherein the at least one non-transitory computer-readable storage medium stores instructions which, when executed by the one or more processors, cause the system to:

receive, from at least one of the one or more internal user devices, a selection of an entry associated with at least one of the one ort more external user devices and a selection of content to the transmitted to the at least one of the one or more external user devices; and transmit the content for delivery to at least one of the one or more external user devices via the messaging service.

18. The system of claim 17, wherein the transmitting of the content for delivery to the at least one of the one or more external user devices comprises transmitting the content from the message database.

19. The system of claim 12, wherein the registration information for the new external user device is a medical record number (MRN) for a patient associated with the new external user device.

20. A non-transitory computer readable storage medium comprising;

instructions stored thereon which, when executed by one or more processors, cause the one or more processors to:

provide a device database that is configured to store information associated with one or more internal user devices or one or more external user devices;

provide a message database that is configured to store prepared communications for external users or to record communications to external users;

provide an internal user interface that is configured to communicate with the one or more internal user devices and to provide a dashboard interface to the one or more internal user devices;

provide a messaging service that is configured to handle communications between the secure communication system and the one or more internal user devices or the one or n ore external user devices;

provide an external user data service configured to store or obtain external user information;

receive, from at least one of the one or more internal user devices via the dashboard interface, registration information for a new external user device;

store the registration information for the new external user device in an entry for the new external user device in the device database;

generate a unique identifier associated with the registration information for the new external user device;

receive, from the new external user device via the messaging service, a communication including the unique identifier and contact information;

identify the entry for the external user from a plurality of entries in the device, database based on the unique identifier;

enable, based on the identifying, communications between one or more internal user devices to the new external user device by storing the contact information in the entry for the new external user device in the device database;

determine groupings of the one or more external network devices based on external user location, external user need for assistance, registered external users that have received assistance, external users that have not yet registered or external users that are in the process of registering; and send via the dashboard interface to at least one of the one or more internal network devices information describing one or more groupings of the one or more external network devices, wherein the as interface is capable of receiving from at least one of the one or more internal network devices a selection of at least one of the one or more groupings of the one or more external network devices.

* * * * *